United States Patent
Pol

(10) Patent No.: US 8,921,120 B2
(45) Date of Patent: Dec. 30, 2014

(54) METHOD FOR DETERMINATION OF MACROMOLECULAR MULTIMERS

(75) Inventor: Ewa Pol, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 160 days.

(21) Appl. No.: 13/503,391

(22) PCT Filed: Oct. 22, 2010

(86) PCT No.: PCT/SE2010/051148
§ 371 (c)(1),
(2), (4) Date: Apr. 23, 2012

(87) PCT Pub. No.: WO2011/049530
PCT Pub. Date: Apr. 28, 2011

(65) Prior Publication Data
US 2012/0208298 A1  Aug. 16, 2012

(30) Foreign Application Priority Data

Oct. 23, 2009 (SE) ..................... 0901374

(51) Int. Cl.
*G01N 33/566* (2006.01)
*C07K 1/14* (2006.01)
*G01N 33/543* (2006.01)

(52) U.S. Cl.
CPC ............ *C07K 1/14* (2013.01); *G01N 33/54373* (2013.01)
USPC ........................................................ 436/501

(58) Field of Classification Search
None
See application file for complete search history.

(56) References Cited

FOREIGN PATENT DOCUMENTS

| GB | WO 2008/114003 A1 * | 9/2008 | ........... G01N 33/543 |
|---|---|---|---|
| WO | 02/001230 | 1/2002 | |
| WO | WO 2008/114003 | 9/2008 | |

OTHER PUBLICATIONS

Pol et al. ("Biosensor-based characterization of serum antibodies during development of an anti-IgE immunotherapeutic against allergy and asthma" J. Mol. Recognit. 2007; 20: 22-31 Published online Oct. 11, 2006).*
Chavane et al. ("At-line quantification of bioactive antibody in bioreactor by surface plasmon resonance using epitope detection" Analytical Biochemistry, 378, 2008, 158-165).*
Sigmundsson, K., et al., Biochemistry, 41:8263-8276 (2002).
EP10825301.4 Search report dated Sep. 4, 2013.

* cited by examiner

Primary Examiner — Ann Lam

(57) ABSTRACT

A method of determining multimers of a macromolecule monomer in a sample containing the macromolecule comprises the steps of (i) determining the total concentration of macromolecule in the sample, (ii) determining by a biosensor-based detection method, especially mass-sensing, the active concentration of macromolecule in the sample, wherein physical characteristics of the macromolecule monomer are used, (iii) comparing the relationship of determined active macromolecule concentration to total macromolecule concentration for the sample with a corresponding relationship for an at least substantially multimer-free macromolecule-containing sample, and (iv) from a resulting difference determining the presence of multimers in the sample. The method may be used in the purification of macromolecules, such as proteins.

7 Claims, 3 Drawing Sheets

METHOD FOR DETERMINATION OF MACROMOLECULAR MULTIMERS

CROSS-REFERENCE TO RELATED APPLICATIONS

This application is a filing under 35 U.S.C. 371 of international application number PCT/SE2010/051148, filed Oct. 22, 2010, published on Apr. 28, 2011 as WO 2011/049530, which claims priority to application number 0901374-9 filed in Sweden on Oct. 23, 2009.

FIELD OF THE INVENTION

The present invention relates a method for determining the presence of multimers, such as dimers or trimers, of a macromolecule in a sample. The invention also relates to the use of the method in the purification of macromolecules.

BACKGROUND OF THE INVENTION

Bio-macromolecules, such as proteins, nucleic acids and polysaccharides, may often partially occur in the form of multimers, such as dimers, trimers or higher oligomers or aggregates. In, for example, recombinant DNA technology, where desired polypeptides or proteins are produced in host organisms and isolated from cell extracts under conditions and in concentrations quite different from those in their natural environment, the conditions may favour the formation of such multimers through intermolecular disulphide linkages or other covalent bonds, or through non-covalent interactions.

The presence of such multimers of a target macromolecule are many times undesired. For instance, if the macromolecule is intended for therapeutic use, the multimeric forms of the macromolecule may have lower or lack the biologic activity, or even cause undesired side-effects.

Prior art methods for analyzing protein or peptide multimers in a sample include, for example, size-exclusion chromatography and immunoassays. Whereas size-exclusion chromatography is relatively slow and complex to perform, the immunoassays require the use of specific monoclonal antibodies to the target proteins or peptides.

There is therefore a need for a method which can conveniently and rapidly analyse the presence of multimers of bio-macromolecules, for example in the purification of proteins or peptides, or when optimizing the conditions for protein purification.

In a solution of a biomolecule, such as a protein or peptide, not all biomolecules may have the expected activity, i.e. the ability to interact specifically with one particular ligand. For instance, a protein prepared by genetic engineering may have molecules incorrectly folded, or protein molecules may have been damaged during purification. Therefore, in a biological context it is the biologically active concentration that is relevant rather than the total concentration of the protein which merely indicates the amount of the biomolecule per unit volume.

Whereas the total concentration of e.g. a protein is typically measured by UV or NIR absorption spectrometry (which does not distinguish between active and inactive molecules), the active concentration of a biomolecule may conveniently be measured by biosensor technology, wherein a sample containing the biomolecule is contacted with a sensor surface with a specific ligand immobilized thereon, and the association/dissociation process at the surface is monitored.

In the determination of active concentration using biosensor technology, analyte concentrations can be determined without reference to a calibration standard. This method, which is usually referred to as Calibration-Free Concentration Analysis (CFCA), relies upon measurement of analyte binding to a target immobilized on a sensor surface at varying flow rates under conditions where the observed rate of binding is partially or completely limited by transport of analyte molecules to the sensor surface, i.e. partially or completely controlled by diffusion.

It is an object of the present invention to provide a method for analysing macromolecule multimers using such a sensor-based method for active concentration determination.

SUMMARY OF THE INVENTION

According to the present invention, active concentration measurement by a sensor of mass-sensing type may be used to detect the presence of and analyse the composition of multimers of a macromolecule, typically a biomacromolecule such as a protein or polypeptide. This approach is based on the fact that when macromolecules are bound to the sensor surface of a mass-sensing biosensor, the sensed mass change does not differentiate between monomers and oligomeric forms of the macromolecule, if both forms bind to the surface, and the mass on the sensor surface does therefore not change if multimers of the macromolecule are present. The molecular weight, the diffusion coefficient and the molar concentration of the macromolecule are, however, altered, and if these physical characteristics of the macromolecule monomer are used when calculating the active concentration, the determined active concentration for a sample which contains e.g. dimeric or trimeric forms of the macromolecule will be lower than it would have been for a sample containing only the monomeric form. In other words, the active concentration may be said to be underestimated, the degree of underestimation being correlable to the composition of the sample.

In one aspect, the present invention provides a method of determining the presence of multimers of a macromolecule in a sample containing the macromolecule, comprising the steps of (i) determining the total concentration of macromolecule in the sample, (ii) determining by a biosensor-based detection method, especially mass-sensing, the active concentration of macromolecule in the sample, wherein physical molecular characteristics of the macromolecule monomer are used, (iii) comparing the relationship of determined active macromolecule concentration to total macromolecule concentration for the sample with a corresponding relationship for an at least substantially multimer-free macromolecule-containing sample, and (iv) from a resulting difference determining the presence of multimers in the sample.

The physical molecular characteristics of the macromolecule typically include the molecular weight (Mw) and the diffusion coefficient (D).

The relationship between active macromolecule and the total concentration of macromolecule is typically the "activity" of the sample with regard to active macromolecule, defined as the ratio of active concentration to total concentration.

Preferably, this relationship for the multimer-free sample is obtained by performing a corresponding determination of total concentration and active concentration for such a sample as well, i.e. providing a sample containing macromolecule monomer which is at least substantially free from multimers, determining the total macromolecule concentration thereof, and determining the active concentration of macromolecule monomer in the sample using the mass-sensing-based detection method.

The determination of active concentration preferably comprises contacting the sample with a sensor surface at varying flow rates under conditions of at least partial mass transport limitation, especially without the use of a calibration standard, i.e. in a calibration-free format.

The macromolecule is preferably a bio-macromolecule, particularly selected from proteins (including e.g. antibodies), polypeptides and nucleic acids.

In another aspect, the present invention provides the use of the method in the purification of a macromolecule.

Further preferred embodiments of the invention are set forth in the dependent claims.

A more complete understanding of the present invention, as well as further features and advantages thereof, will be obtained by reference to the following detailed description and the accompanying drawings.

DETAILED DESCRIPTION OF THE INVENTION

Figure 1:
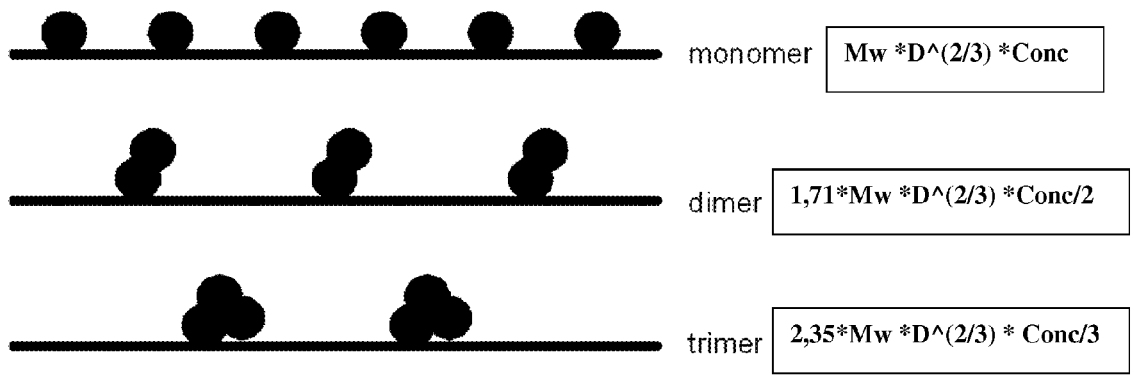
FIG. 1 is a schematic illustration of monomers, dimers and trimers of a macromolecule binding to a sensor surface.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

As mentioned above, the present invention relates to the detection and analysis of multimeric forms of a macromolecule in a sample. In brief, the method is based on determining the active concentration of the macromolecule using a biosensor detection technology, especially mass-sensing, and determining from the relationship of active concentration to total concentration determining the presence and optionally the composition of multimeric forms of the macromolecule.

A biosensor is typically based on label-free techniques, detecting a change in a property of a sensor surface, such as mass, refractive index or thickness of the immobilized layer. Typical biosensors for the purposes of the present invention are based on mass detection at the sensor surface and include especially optical methods and piezoelectric or acoustic wave methods. Representative sensors based on optical detection methods include those that detect mass surface concentration, such as sensors based on reflection-optical methods, including e.g. evanescent wave-based sensors including surface plasmon resonance (SPR) sensors; frustrated total reflection (FTR) sensors, and waveguide sensors, including e.g. reflective interference spectroscopy (RIfS) sensors. Piezoelectric and acoustic wave sensors include surface acoustic wave (SAW) and quartz crystal microbalance (QCM) sensors.

Biosensor systems based on SPR and other detection techniques are commercially available today. Exemplary such SPR-biosensors include the flow-through cell-based Biacore® systems (GE Healthcare Bio-Sciences AB, Uppsala, Sweden) and ProteOn™ XPR system (Bio-Rad Laboratories, Hercules, Calif., USA) which use surface plasmon resonance for detecting interactions between molecules in a sample and molecular structures immobilized on a sensing surface. As sample is passed over the sensor surface, the progress of binding directly reflects the rate at which the interaction occurs. Injection of sample is usually followed by a buffer flow during which the detector response reflects the rate of dissociation of the complex on the surface. A typical output from the system is a graph or curve describing the progress of the molecular interaction with time, including an association phase part and a dissociation phase part. This binding curve, which is usually displayed on a computer screen, is often referred to as a "sensorgram".

With the Biacore® systems it is thus possible to determine in real time without the use of labeling, and often without purification of the substances involved, not only the presence and concentration of a particular molecule, or analyte, in a sample, but also additional interaction parameters, including kinetic rate constants for association (binding) and dissociation in the molecular interaction as well as the affinity for the surface interaction.

In the following, the present invention will to a large extent be described, for illustration only and no limitation, with regard to SPR-sensors of the Biacore® system type.

The Biacore® systems, as well as analogous sensor systems, measure the active analyte concentration as distinct from the total concentration of the analyte. As to the term "active", it is the choice of ligand on the sensor surface that defines the kind of activity being measured. While e.g. standard protein concentration analysis using a calibration curve may be used, the Biacore® systems (and analogous sensor systems) permits assessment of protein (and other macromolecule) concentration by a calibration-free method, which is often referred to as calibration-free concentration analysis (CFCA).

The method relies on changes in binding rates of analyte to a target (ligand) immobilized on a surface with varying flow rates under conditions of partial or total mass transport and does, as mentioned, not require standards of known concentrations, given that the molecular mass of the molecule of interest is known. For a more detailed description such calibration-free measurement it may be referred to, for example, Sigmundsson, K. et al. (2002) Biochemistry 26, 8263-8276.

In Biacore® instruments, or analogous instruments, samples are injected in a micro-flow system and transported in a laminar flow to the sensor surface. Molecules reach the sensor surface from bulk solution by a diffusion-controlled transport process. In addition to the concentration of analyte molecules, factors influencing the transport include the diffusion coefficient, flow cell dimensions and flow rate. The balance between the transport rate and the binding rate determines whether the observed binding will be transport limited or reaction limited.

For successful CFCA, the observed binding rate must be at least partially limited by transport. The concentration is obtained by running the binding experiments at least two different flow rates and fitting the data to a model describing the process, e.g. a two-compartment model (Myszka, D. G., et al. (1998) Biophys. J. 75, 583-594, and Schank-Retzlaff, M. L. and Sligar, S. G. (2000) Anal. Chem. 72, 4212-4220). For a more comprehensive description of curve fitting with regard to the Biacore® systems, it may be referred to the BIAevaluation™ Software Handbook (GE Healthcare Bio-Sciences AB, Uppsala, Sweden).

The binding of analyte to surface-attached ligand in a controlled flow system is represented by the sum of two process, transport of analyte to the surface and molecular interaction with the ligand. The molecular interaction is described by the rate constants $k_a$ and $k_d$, while transport of analyte to and from the surface is described by the mass transport constants $k_m$ and $k_{-m}$ (also referred to as $k_t$ and $k_{-t}$). The transport phenomenon is symmetrical since this is essentially a diffusion-limited process, so $k_m = k_{-m}$.

Thus, for determining active concentration of a protein, for example, using a Biacore® system (or analogous), a protein solution is injected at least twice over the surface with immobilized interaction partner. The binding phases of the sensorgrams obtained from such an experiment are fitted to a bi-molecular interaction model with mass transfer term, in which the active concentration is a fitted parameter. The fitting is preferably global, i.e. the interaction model is fitted simultaneously to multiple binding curves (sensorgrams). In this model, the value of the mass transport coefficient is introduced as a constant, which, as described above, may be calculated from the dimensions of the flow cell, the diffusion coefficient of the protein and the flow rate used.

In a simplified form, the response increase dR/dt at the sensor surface given by bound protein is proportional to the mass transport constant $k_t$ and the active concentration, i.e.

$$dR/dt = k_t * (\text{active concentration}) \quad (2)$$

$k_t$ can be re-written as "constant*Mw*$D^{2/3}$", where Mw is the molecular weight of the protein and D is its diffusion coefficient, which gives $$dR/dt = \text{const} * Mw * D^{2/3} * (\text{active concentration}) \quad (3)$$

The diffusion coefficient D is a function of the size and shape of the molecule and the frictional resistance offered by the viscosity of the solvent in question. For spherical molecules, the diffusion coefficient is inversely proportional to the radius and thus proportional to the cube root of the molecular weight. For very large solute molecules, such as proteins, however, the diffusion coefficient os relatively insensitive to the molecular weight.

When protein molecules aggregate to form makes dimers, trimers and so on, the mass on the sensor surface does not change, whereas Mw, D, Mw*$D^{2/3}$ and the molar concentration are altered. Since the decrease of molar concentration with the number of subunits is greater than the increase of Mw*$D^{2/3}$, the determined active concentration being based on these physical parameters for the protein monomer will decrease. That is, the active concentration as determined for a sample which contains e.g. dimeric or trimeric forms of the protein will be lower than it would have been for a sample containing only the monomeric form. The active concentration may therefore be said to be "underestimated". The degree of such underestimation may be correlated to the composition of multimers in the sample.

This is shown in Table 1 below, where the overall effect on concentration determination, and thereby the "underestimation" of active concentration, has been calculated for a protein (Mw 12500) and dimers, trimers, etc up to multimers of eight subunits. The calculations were performed assuming that the molecular shape of multimer does not change compared to the monomeric molecule and that binding of multimer occurs under mass transport limited conditions.

TABLE 1

| Mw (kDa) | D ($m^2/s$) | $D^{2/3}$ | Mw * $D^{2/3}$ | Sub-units | Mw * $D^{2/3}$ increase | Molar conc. decrease | Overall effect | Under-estimation |
|---|---|---|---|---|---|---|---|---|
| 12.5 | 1.2E−10 | 2.4E−07 | 3.0E−03 | 1 | 1.00 | 1.00 | 1.00 | 0.00 |
| 25.0 | 9.2E−11 | 2.0E−07 | 5.1E−03 | 2 | 1.71 | 0.50 | 0.86 | 14.25 |
| 37.5 | 8.1E−11 | 1.9E−07 | 7.0E−03 | 3 | 2.35 | 0.33 | 0.78 | 21.64 |
| 50.0 | 7.3E−11 | 1.8E−07 | 8.8E−03 | 4 | 2.94 | 0.25 | 0.74 | 26.49 |
| 62.5 | 6.8E−11 | 1.7E−07 | 1.0E−02 | 5 | 3.50 | 0.20 | 0.70 | 30.05 |
| 75.0 | 6.4E−11 | 1.6E−07 | 1.2E−02 | 6 | 4.03 | 0.17 | 0.67 | 32.83 |
| 87.5 | 6.1E−11 | 1.5E−07 | 1.4E−02 | 7 | 4.54 | 0.14 | 0.65 | 35.09 |
| 100.0 | 5.8E−11 | 1.5E−07 | 1.5E−02 | 8 | 5.04 | 0.13 | 0.63 | 36.99 |

This is further illustrated in FIG. 1, showing that the mass on the surface does not change when a protein forms multimers (the immobilized interaction partner, or ligand, is omitted in the Figure), whereas the product Mw$D^{2/3}$ increases and the concentration decreases.

According to the present invention, this decrease of active concentration measured as above when multimers are formed may be used for their detection, and also to find out the composition of a sample containing multimers.

It is understood that the method can be used when the multimer retains the binding capacity to the ligand on the sensor surface and the conditions for mass transport limitation are maintained. It is not, however, necessary that the kinetics and the affinity of interaction between ligand and monomer, and ligand and multimer are the same. In addition, at least a monomer standard should be available.

The underestimation of concentration increases when:
the molecular shape of multimer (expressed as fractional ratio. f/f0) increases,
the binding of multimer occurs without mass transport limitation (much weaker binding),
the multimer does not bind.

Determination of the presence of multimers of a macromolecule, such as a protein, according to the invention may be performed as follows.

1. Determine the total concentration of a monomer and of samples of unknown composition (containing multimers), respectively. This may typically be accomplished by UV absorption spectroscopy, e.g. at 280 nm.

2. Determine the active concentration of a monomer and samples containing multimers, respectively.

3. Calculate the activity of the monomer=active concentration/total concentration.

4. Calculate the activity of samples containing multimers=active concentration/total concentration.

5. Compare the determined activity of monomer to that of the sample with unknown composition. (See last two columns in Table 1 above.)

The composition of the sample can be determined with higher precision if besides a monomer standard, a multimer standard is also available.

Figure 2:
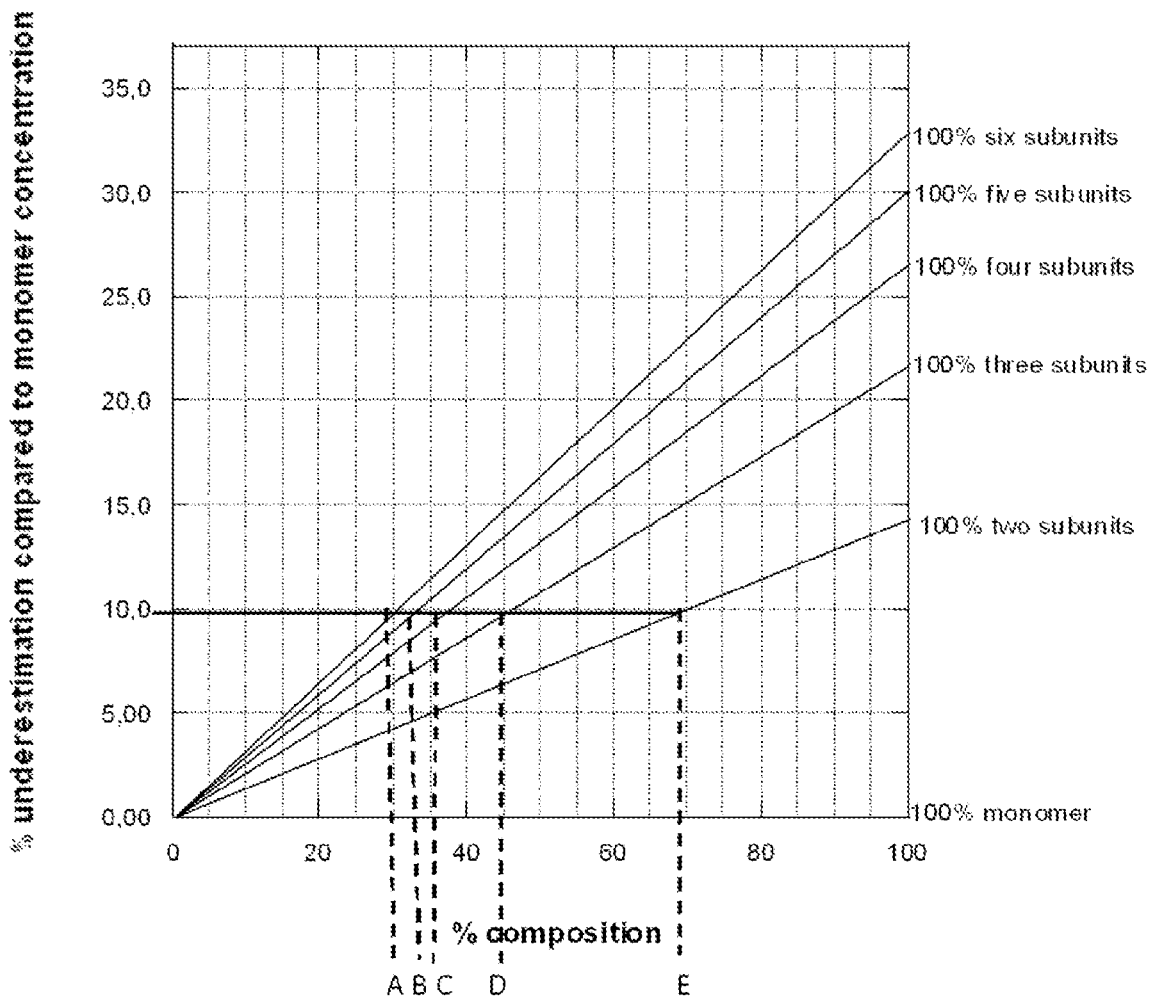
FIG. 2 is a diagram of percent "underestimation" compared to monomer concentration of active concentration versus percent monomer for compositions of varying numbers of macromolecule subunits. The calculations were performed assuming that the molecular shape of multimer does not change compared to the monomeric molecule and that binding occurs under mass transport limited conditions.

In a simplified method, the value of initial binding slope, giving a relative activity, can be used instead of active concentration As mentioned above, it is also possible to correlate the degree of "underestimation" or decrease of activity to the sample composition as illustrated in FIG. 2, which shows an example of how the composition of an unknown sample may be analysed.

Thus, with reference to FIG. 2, if the "underestimation" of the monomer concentration is about 10%, the possible sample composition can be as follows, assuming that the sample contains two components: monomer and one form of multimer:

A=28% hexamer, 100-28% monomer

B=33% pentamer, 100-33% monomer

C=36% tetramer, 100-36% monomer

D=44% trimer, 100-44% monomer

E=68% dimer, 100-68% monomer.

In the following Example, an experiment showing the determination of multimers in a sample of unknown composition (with regard to the presence of multimers) is described.

EXAMPLE

A Biacore® 3000 instrument (GE Healthcare Bio-Sciences AB, Uppsala, Sweden) was used. In this instrument, a micro-fluidic system passes samples and running buffer through four individually detected flow cells (one by one or in series). As sensor chip was used Series S sensor Chip CM5 (GE Healthcare Bio-Sciences AB, Uppsala, Sweden) which has a gold-coated surface with a covalently carboxymethyl-modified dextran polymer hydrogel. For calculations, the instrument dedicated BIAevaluation software (GE Healthcare Bio-Sciences AB, Uppsala, Sweden) was used.

The outputs from the instrument via the instrument control software are "sensorgrams" which are plots of detector response (measured in "resonance units", RU) as a function of time. An increase of 1000 RU corresponds to an increase of mass on the sensor surface of approximately 1 ng/mm².

Two antibody samples were provided, (i) a sample containing monomeric antibody, and (ii) a sample of "unknown composition" as to the presence of multimers of the antibody.

The total concentration of both samples were determined by UV absorption spectroscopy at 280 nm.

The samples were then diluted 200 times, and the active concentration of each sample was determined by calibration-free active concentration analysis (CFCA), using the Biacore® 3000 instrument with anti-human IgG immobilized on the sensor chip.

Figure 3:
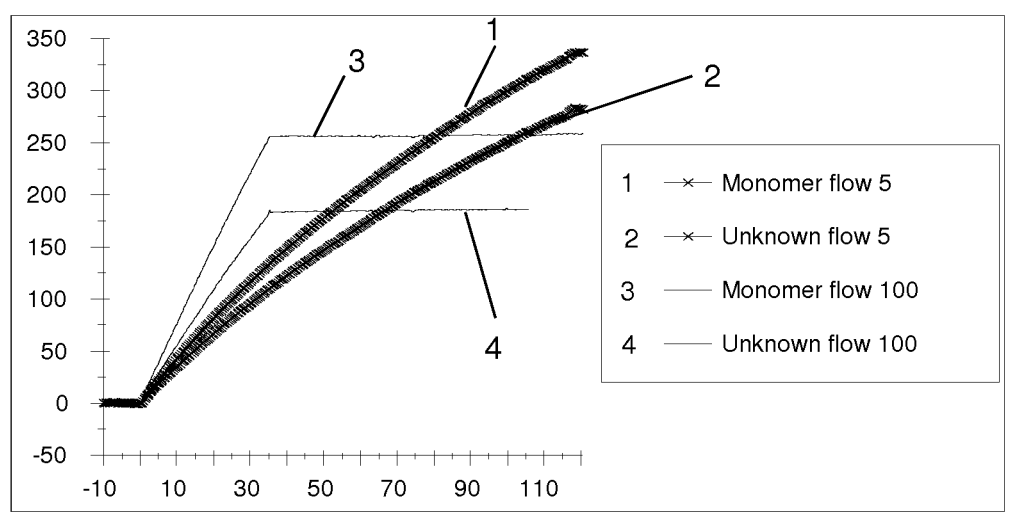
FIG. 3 is an overlay plot of sensorgrams obtained in the determination of active concentrations in an embodiment of the method according to the present invention.

The antibody solutions were injected at two flow rates, 5 and 100 μl/min, and the sensorgrams were evaluated using a 1:1 binding model with a mass transport term for the determination of active concentration. An overlay plot of all sensorgrams obtained is shown in FIG. 3, where the y-axis is the response in RU and the x-axis is time in seconds.

In the CFCA-calculation by the BIAevaluation™ software, the following constants were used, all relating to the antibody monomer form.

| | |
|---|---|
| D (25° C.) (m²/s): | 4.58E−11 |
| $k_m$ flow 5 μl/min (RU/M * s): | 1.62E+09 |
| $k_m$ flow 100 μl/min (RU/M * s) | 4.40E+09 |

The results are presented in Table 2 below.

TABLE 2

| Sample | A280 | Conc. from A280 (M) | Conc. of 1/200 dilution (M) | Conc. by CFCA (M) | % Activity | % Under-estimation |
|---|---|---|---|---|---|---|
| Monomer | 0.350 | 1.67E−06 | 8.37E−09 | 3.31E−09 | 40 | |
| Unknown | 0.357 | 1.71E−06 | 8.54E−09 | 3.00E−09 | 35 | 12.5 |

As a comparison, the compositions of the two samples were also analyzed by size exclusion chromatography (SEC) on Sephadex® 200 (GE Healthcare Bio-Sciences AB, Uppsala, Sweden). The results are shown in Table 3 below.

TABLE 3

| Sample | % Monomer | % Dimer |
|---|---|---|
| Monomer | 99.7 | 0.30 |
| Unknown | 2.82 | 97.18 |

According to these results, the expected % "underestimation" of active concentration should be 14%, which is 1.5% more than obtained by CFCA (12.5%). This discrepancy may depend on several factors. One possible reason may be that no consideration has been given to the change of the molecular shape.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A method of determining the presence of multimers of a macromolecule monomer in a sample containing the macromolecule, comprising the steps of:
   determining the total concentration of the macromolecule in the sample;
   determining the active concentration of the macromolecule in the sample by putting the sample in contact with a sensor surface of a biosensor system arranged to perform a biosensor-based detection method, wherein physical characteristics of the macromolecule monomer are used to determine the active concentration;
   providing a reference value for the active concentration of a monomer-standard reference-sample with a total concentration of the macromolecule corresponding to the total concentration of the macromolecule determined for the sample
   comparing the determined active concentration of the macromolecule in the sample with the reference value for the active concentration of the monomer reference-sample; and
   wherein a lower active concentration of the macromolecule in the sample compared to the reference value for the active concentration of the monomer reference-sample provides a measure of the presence and level of multimers in the sample.

2. The method of claim 1, wherein the biosensor-based detection method comprises mass-sensing.

3. The method of claim 1, wherein the physical characteristics comprise molecular weight and diffusion coefficient.

4. The method of claim 1, wherein the determination of active concentration comprises contacting the sample with a sensor surface at varying flow rates under conditions of at least partial mass transport limitation.

5. The method of claim 4, wherein the determination is performed without the use of a calibration standard.

6. The method of claim 1, wherein the method is based on evanescent wave sensing, preferably surface plasmon resonance (SPR).

7. The method of claim 1, wherein the macromolecule is selected from the group consisting of proteins, polypeptides and nucleic acids.

\* \* \* \* \*